(12) United States Patent
Yasushi et al.

(10) Patent No.: US 11,238,718 B2
(45) Date of Patent: Feb. 1, 2022

(54) VIBRATION CONTROL DEVICE

(71) Applicants: PIONEER CORPORATION, Tokyo (JP); PIONEER SYSTEM TECHNOLOGY CORPORATION, Sendai (JP)

(72) Inventors: Mitsuo Yasushi, Kawagoe (JP); Yoshikazu Takeuchi, Kawagoe (JP); Kazumi Sugaya, Kawagoe (JP); Kota Kakisaka, Kawagoe (JP); Kenta Isozaki, Kawagoe (JP); Takashi Morishige, Kawagoe (JP); Takashi Iizawa, Kawagoe (JP); Naoki Murakami, Kawagoe (JP); Tatsuya Fukuda, Kawagoe (JP)

(73) Assignees: PIONEER CORPORATION, Tokyo (JP); PIONEER SYSTEM TECHNOLOGY CORPORATION, Miyagi (JP)

( * ) Notice: Subject to any disclaimer, the term of this patent is extended or adjusted under 35 U.S.C. 154(b) by 0 days.

(21) Appl. No.: 17/051,194

(22) PCT Filed: Apr. 18, 2019

(86) PCT No.: PCT/JP2019/016591
§ 371 (c)(1),
(2) Date: Oct. 28, 2020

(87) PCT Pub. No.: WO2019/211990
PCT Pub. Date: Nov. 7, 2019

(65) Prior Publication Data
US 2021/0241596 A1 Aug. 5, 2021

(30) Foreign Application Priority Data
May 1, 2018 (JP) .............................. JP2018-088179

(51) Int. Cl.
*G08B 21/06* (2006.01)
*G08B 6/00* (2006.01)

(52) U.S. Cl.
CPC ............... *G08B 21/06* (2013.01); *G08B 6/00* (2013.01)

(58) Field of Classification Search
CPC ........ G01M 7/022; G01S 13/765; G01S 1/02; G01S 7/04; G01S 7/4065; G01V 1/245;
(Continued)

(56) References Cited

U.S. PATENT DOCUMENTS

| 6,087,942 A * | 7/2000 | Sleichter, III ............ B60N 2/56 340/576 |
| 6,993,380 B1 * | 1/2006 | Modarres .............. A61B 5/4806 600/544 |

(Continued)

FOREIGN PATENT DOCUMENTS

| JP | 2000-225877 | 8/2000 |
| JP | 2018-55527 | 4/2018 |
| WO | 2013/186902 | 12/2013 |

OTHER PUBLICATIONS

International Search Report for PCT/JP2019/016591 dated May 28, 2019, 3 pages.
(Continued)

*Primary Examiner* — Daniel Previl
(74) *Attorney, Agent, or Firm* — Nixon & Vanderhye

(57) ABSTRACT

A vibration control device is provided which enables an awakening effect for a user to be increased while making it difficult to give discomfort to the user. A harmonic signal generating section of a vibration control device is configured to successively output a plurality of alternating signals for driving a vibration unit. By way of the plurality of alternating signals which is successively output and has a frequency ratio represented with a predetermined integer ratio, vibration generated with the plurality of alternating signals can more easily awaken a user while making it difficult to give discomfort to the user.

16 Claims, 7 Drawing Sheets

(58) Field of Classification Search
CPC ........... G02B 30/24; G09G 2320/0261; G09G 3/3406; H01G 7/026; H03B 29/00; H04Q 3/00; H04Q 5/00; H04R 17/00; H04R 17/04; H04R 23/00; Y10S 73/03; Y10S 73/04; Y10S 84/24; Y10T 29/42
USPC ......... 340/575, 568.1, 573.3, 582, 641, 683, 340/667, 693.8, 825.27
See application file for complete search history.

(56) References Cited

U.S. PATENT DOCUMENTS

| | | | | |
|---|---|---|---|---|
| 8,693,286 | B1* | 4/2014 | Rogers | G01S 5/30 |
| | | | | 367/100 |
| 10,130,766 | B1* | 11/2018 | Bibian | A61B 5/369 |
| 10,842,932 | B1* | 11/2020 | Bibian | A61P 21/02 |
| 2002/0140215 | A1* | 10/2002 | Breed | G01S 7/4802 |
| | | | | 280/735 |
| 2010/0312722 | A1* | 12/2010 | Moore | G06Q 99/00 |
| | | | | 705/500 |
| 2011/0015468 | A1* | 1/2011 | Aarts | A61B 5/486 |
| | | | | 600/26 |
| 2012/0182136 | A1* | 7/2012 | Nakayama | B60Q 5/008 |
| | | | | 340/425.5 |
| 2020/0294401 | A1* | 9/2020 | Kerecsen | G05D 1/0287 |

OTHER PUBLICATIONS

Written Opinion of the ISA for PCT/JP2019/016591 dated May 28, 2019, 4 pages.

* cited by examiner

VIBRATION CONTROL DEVICE

This application is the U.S. national phase of International Application No. PCT/JP2019/016591 filed Apr. 18, 2019 which designated the U.S. and claims priority to JP Patent Application No. 2018-088179 filed May 1, 2018, the entire contents of each of which are hereby incorporated by reference.

BACKGROUND OF THE INVENTION

Technical Field

The present invention relates to a vibration control device configured to control a vibration unit.

Background Art

A moving body, such as a vehicle, may be provided with a sensor and an alarm device so that it is configured to generate an alert to a passenger (particularly a driver) when an approach of an obstacle (e.g. another vehicle, an object installed at a road, a pedestrian) has been detected. For generating the alert in this manner, it is proposed to use a vibration body (vibration unit) for generating vibration (e.g. see Patent Document 1).

In a notification system according to Patent Document 1, two vibration bodies are arranged in a seat cushion (seat surface section) of a vehicle seat apparatus, and one vibration body is arranged in a seat back (backrest portion) of the vehicle seat apparatus, the vehicle seat apparatus constituting a seat, wherein they are controlled. In performing the control, it is configured to select one or more of the vibration bodies to be vibrated depending on a direction of approach of the obstacle in order to cause the passenger to recognize from which direction the obstacle is approaching.

CITATION LIST

Patent Literature

Patent Document 1: JP 2000-225877 A

SUMMARY OF THE INVENTION

As another method of utilizing the vibration unit which is installed e.g. in a seat, in addition to Patent Document 1, it is conceivable to use the vibration unit for suppressing drowsiness of a user. This means that the user can be awakened by applying stimulation to the user (driver) by means of vibration. For applying stimulation to the user in such a manner, an awakening effect is increased if stronger stimulation is applied e.g. by generating random vibration and/or increasing the amplitude. However, if stronger stimulation is simply generated, it may give discomfort to the user more easily.

Therefore, one example for objectives of the present invention is to provide a vibration control device which enables the awakening effect for the user to be increased while making it difficult to give discomfort to the user.

In order to achieve the objective, a vibration control device according to the present invention as defined in claim 1 is configured to control a vibration unit which is configured to generate vibration to be transferred to a user, wherein the vibration control device is includes an output section configured to successively output each of a plurality of alternating signals for driving the vibration unit, wherein the plurality of alternating signals has a frequency ratio for their frequencies, the frequency ratio being represented with a predetermined integer ratio.

A vibration control method according to the present invention as defined in claim 10, wherein a vibration unit is controlled which is configured to generate vibration to be transferred to a user, the method including: an output step for successively outputting each of a plurality of alternating signals for driving the vibration unit, wherein the plurality of alternating signals has a frequency ratio for their frequencies, the frequency ratio being represented with a predetermined integer ratio.

DETAILED DESCRIPTION OF THE PREFERRED EMBODIMENTS

Figure 1:
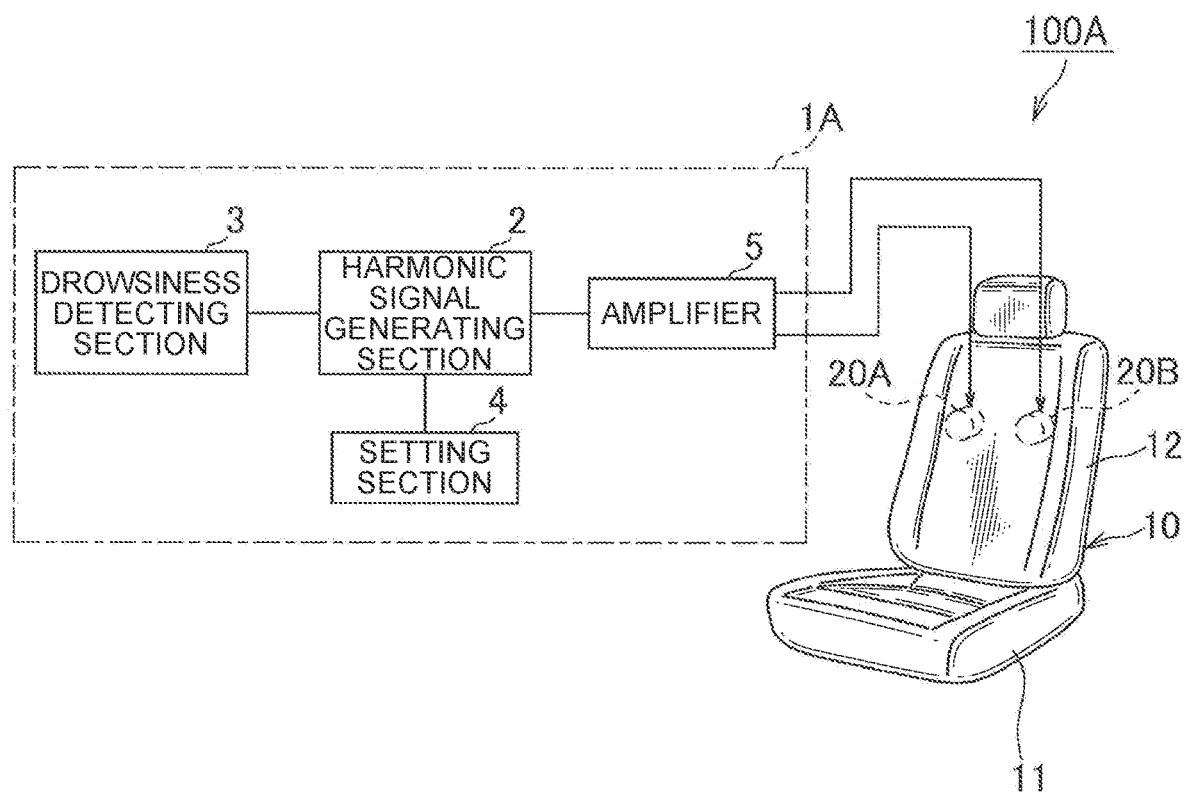
FIG. 1 is a block diagram schematically illustrating a vibration control device according to a first example of the present invention.

Hereinafter, embodiments of the present invention will be described. A vibration control device according to an embodiment of the present invention is configured to control a vibration unit which is configured to generate vibration to be transferred to a user, wherein the vibration control device is includes an output section configured to successively output each of a plurality of alternating signals for driving the vibration unit. For frequencies of the plurality of alternating signals, the plurality of alternating signals has a frequency ratio which is represented with a predetermined integer ratio.

With the vibration control device according to the present embodiment as described above, by means of the plurality of alternating signals which is successively output and has a frequency ratio represented with a predetermined integer ratio, vibration generated with the plurality of alternating signals can more easily awaken a user while making it difficult to give discomfort to the user. This means that it is possible to increase an awakening effect for the user as compared to driving the vibration unit by means of regular signals, such as sinusoidal signals with a single frequency, while it can be more difficult to give discomfort to the user as compared to driving the vibration unit by means of signals with completely random frequencies.

The predetermined integer ratio is preferably a ratio between frequencies of component sounds of a consonance. This means that the vibration unit is preferably driven by means of the plurality of alternating signals which would generate a consonance if they would be input into a speaker.

Preferably, the vibration control device further includes an acquisition section configured to acquire drowsiness information of the user, wherein the output section is configured to output the plurality of alternating signals if the drowsiness information is acquired by the acquisition section. This may enable vibration to be generated as necessary and make it difficult to give discomfort to the user. Additionally, if vibration is generated only when the user feels drowsy, it is possible to suppress that the user gets used to the vibration.

Each of the plurality of alternating signals preferably has a frequency of 40-120 Hz. In this manner, it is possible to achieve an adequate depth of the vibration with which the alternating signals are transferred into a body of the user, which may make it difficult to give discomfort to the user. This means that if the frequency of vibration is too low, the vibration may reach an internal organ of the user's body, which may give discomfort, while if the frequency of vibration is too high, the vibration may rub a skin surface of the user, which may give discomfort as well.

The output section may randomly vary a combination of frequencies of the plurality of alternating signals in time. Further, the output section may output the plurality of alternating signals with a pause period interposed therebetween, wherein a length of the pause period may be randomly varied. As such, with varying the combination of frequencies and/or the length of the pause period, it is possible to suppress that the user gets used to the vibration, which enables the awakening effect to be maintained for a longer time. In case that the plurality of alternating signals having the predetermined integer frequency ratio for their frequencies is configured as a group of harmonic signals, the "pause period" may be defined as a period between a group of harmonic signals and a subsequent group of harmonic signals and may be randomly varied in length. In the case as mentioned above, it is also possible to define the "pause period" as a period between alternating signals which constitute a group of harmonic signals, wherein the length of the pause period may be randomly varied (i.e. a tempo may be randomly varied).

A vibration generating device according to an embodiment of the present invention includes the vibration control device as described above and at least one vibration unit.

The vibration unit may be provided inside a seat surface section or a backrest section of the seat in which the user is seated. Further, the vibration unit may be also installed at another object.

The vibration generating device includes a plurality of vibration units, wherein the output section may output each of a plurality of alternating signals which are correlated to the plurality of vibration units respectively. Furthermore, the vibration generating device may output same alternating signals to the plurality of vibration units.

A vibration control method according to an embodiment of the present invention is a method in which a vibration unit is controlled, the vibration unit being configured to generate vibration to be transferred to a user, the vibration control method including an output step for successively outputting each of a plurality of alternating signals for driving the vibration unit. For frequencies of the plurality of alternating signals, the plurality of alternating signals has a frequency ratio which is represented with a predetermined integer ratio.

Furthermore, the present invention may be implemented as a vibration control program which is configured to cause a computer to execute the vibration control method as described above. In this manner, a computer may be used to enable the awakening effect for the user to be increased while making it difficult to give discomfort to the user.

Moreover, the vibration control program as described above may be stored in a computer-readable storage medium. In this manner, it is possible not only to integrate the program into an equipment, but also put it alone into the market. Furthermore, it facilitates version updating.

EXAMPLES

Hereinafter, examples of the present invention will be described in more details. It is to be noted that for a second example, same components and components with similar functions to those in a first example are indicated with same reference signs as those in the first example, and description is not repeated for such components.

First Example

As shown in FIG. 1, a vibration control device 1A according to the present example includes a harmonic signal generating section 2, a drowsiness detecting section 3 as an acquisition section, a setting section 4 and an amplifier 5, wherein the vibration control device 1A is configured to control two vibration units 20A and 20B which are disposed in a seat 10 of a moving body (vehicle). The vibration control device 1A and the two vibration units 20A, 20B constitute a vibration generating device 100A.

The harmonic signal generating section 2 is a control section which is constituted from a CPU (Central Processing Unit) with a memory, such as RAM (Random Access Memory) and/or ROM (Read Only Memory), wherein the harmonic signal generating section 2 is configured to manage the entire control of the vibration control device 1A. This means that the harmonic signal generating section 2 generates harmonic signals for driving the vibration units 20A and 20B and transmits them to the vibration units 20A and 20B, as described later.

The drowsiness detecting section 3 is configured to acquire drowsiness information of a user, e.g. based on biometric information of the user. For example, it is sufficient if the drowsiness detecting section 3 is configured to measure a heart rate, measure the number of blinks, and/or detect orientation of eyes, etc. It is to be noted that as used in the present example, a user refers to a person sitting in the seat 10. When the seat 10 is a driver seat, the user is a driver of the moving body.

The setting section 4 is a storage device which has information about the harmonic signals stored therein. The harmonic signals include a plurality of alternating signals, wherein each of the plurality of alternating signals is successively output. It is to be noted that a sequence for outputting the plurality of alternating signals may be set in any appropriate manner, wherein they may be output successively in descending order of the frequency, successively output in ascending order of the frequency, or randomly.

The plurality of alternating signals in the harmonic signals has different frequencies from each other, wherein a frequency ratio between the frequencies of the plurality of alternating signals is represented by a predetermined integer ratio. If an audio speaker would be driven by the harmonic signals, the audio speaker would emit a consonance (arpeggio). This means that the frequency ratio between the plurality of alternating signals would be a ratio between frequencies of component sounds of the consonance. It is sufficient if the frequency ratio between the plurality of alternating signals is e.g. 1:2, 2:3, 3:4, 4:5, 5:6, 4:5:6, 10:12:15, and the frequency ratio is represented by a simple integer ratio (e.g. all numbers contained in the ratio are of the order of tens or smaller).

The setting section 4 has various parameters related to the harmonic signals stored therein. Examples for parameters of the harmonic signals include a combination of frequencies, a sequence of outputting the alternating signals, output tempo (a length of a period between alternating signals which form a group of harmonic signals), an output duration of one alternating signal and/or an amplitude of the alternating signals. It is to be noted that the parameters may be adjustable by the user in any appropriate manner, randomly variable, or variable depending on the drowsiness information.

The amplifier 5 is disposed between the harmonic signal generating section 2 and the vibration units 20A, 20B, wherein the amplifier 5 is configured to amplify the harmonic signals output by the harmonic signal generating section 2 in an appropriate manner and to provide them to the vibration units 20A and 20B. Although the harmonic signal generating section 2 and the amplifier 2 according to the present example are configured to function as an output section, the amplifier 5 may be omitted.

According to the present example, two vibration units 20A and 20B are disposed inside a backrest section 12 of the seat 10 and arranged along a vehicle width direction (right-left direction with regard to the sitting person). It is to be noted that the vibration units may be provided in a seat surface section 11 of the seat 10, or may be provided in both of the backrest section 12 and the seat surface section 11. Furthermore, the number of the vibration units may not be limited to two, and one or three or more vibration units may be used.

Figure 2A:
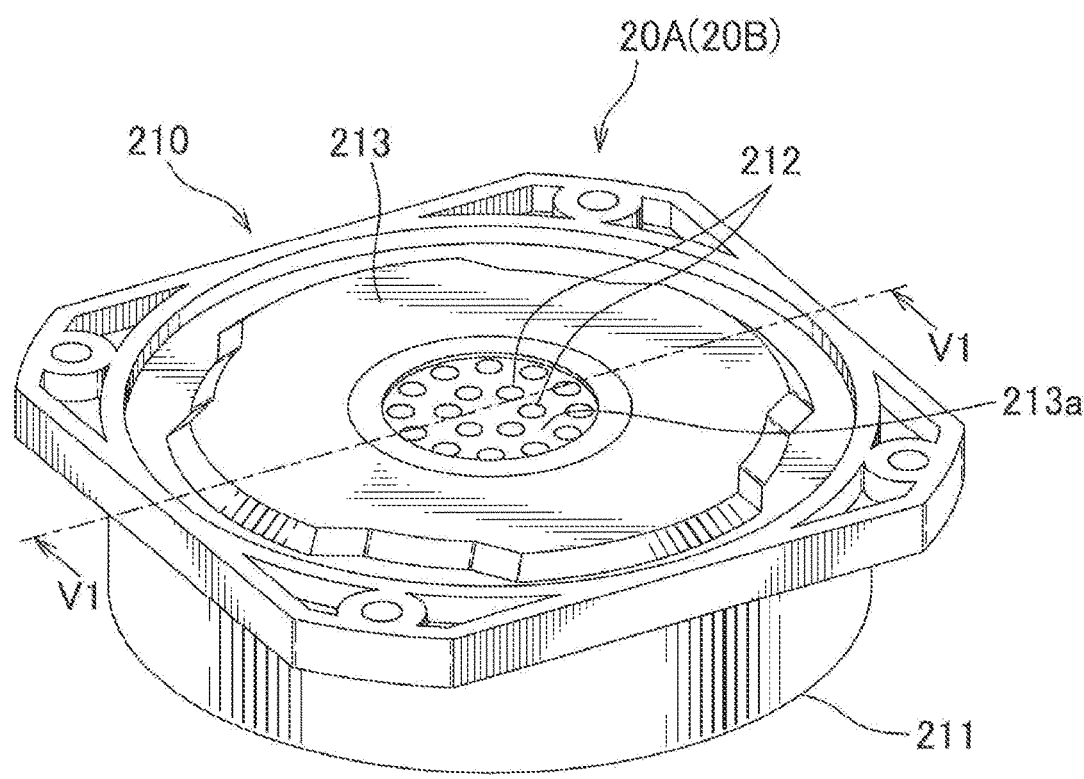
FIG. 2 is a perspective view illustrating a vibration unit to be controlled by the vibration control device.
Figure 2B:
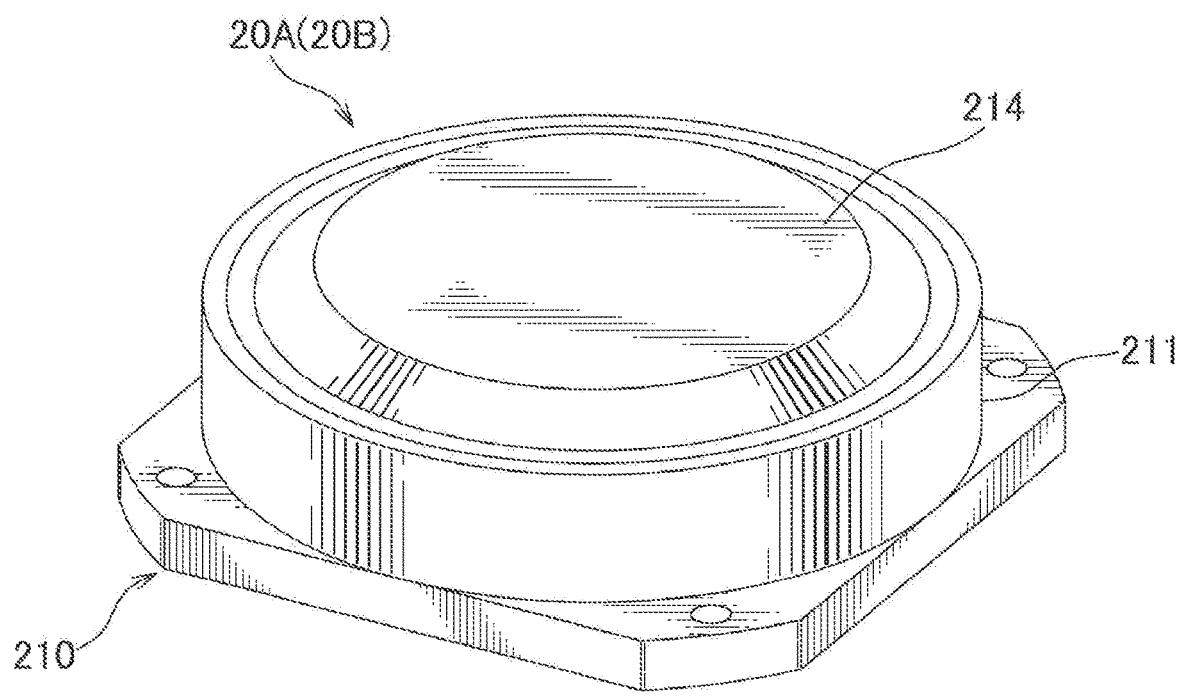
Figure 3:
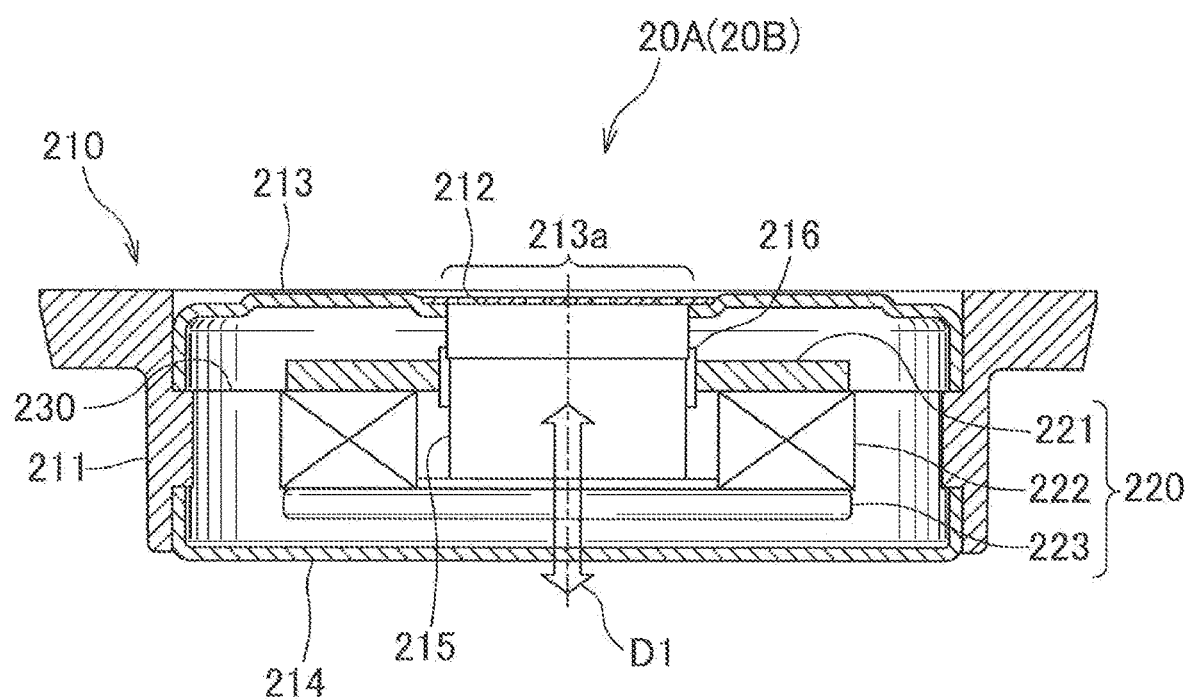
FIG. 3 is a sectional view illustrating the vibration unit.

The vibration units 20A and 20B are configured to generate vibration in a vibration direction and transmit it to a back of the user, the vibration direction being substantially orthogonal to a front surface of the backrest section 11. Here, the vibration units 20A and 20B will be described in more details with reference to FIGS. 2 and 3. FIG. 3 shows a sectional view illustrating a cross section along the cutting line V1-V1 in FIG. 2(A).

Each of the vibration units 20A and 20B is a magnetic circuit 220 accommodated in a casing 210. The casing 210 is a cylindrical frame 211 which is short in a direction of height, wherein the cylindrical frame 211 has an opening on one end side closed with a first circular plate wall 213, the first plate wall 213 having a plurality of through-holes 212 in a middle portion, wherein the cylindrical frame 211 has another opening on the other end side closed with a second circular plate wall 214. FIG. 2(A) shows the vibration units 20A and 20B in a view from the first plate wall 213 side with the through-holes 212, wherein FIG. 2(B) shows the vibration units 20A and 20B in another view from the opposite side.

A cylindrical bobbin 215 extends vertically from a substantially middle portion of the first plate wall 213 toward the second plate wall 214 so as to surround the plurality of through-holes 212, wherein a voice coil 216 is disposed around an outer circumference of the bobbin 215. In this manner, the voice coil 216 is fixed to the first plate wall 213 via the bobbin 215. Further, the plurality of through-holes 212 is disposed in a region 213a which corresponds to the interior of the voice coil 216 in a top view in a direction intersecting the first plate wall 213.

Each magnetic circuit 220 includes a plate 221, a magnet 222 and a yoke 223, wherein the plate 221 and magnet 222 have a ring shape, and the yoke 223 has a circular disc shape. The plate 221 and the magnet 222 are arranged coaxially with a gap to the voice coil 216. The plate 221, and thus the magnetic circuit 220 are supported by an inner wall surface of the cylindrical frame 211 via a damper 230 so as to be capable of vibrating in an approaching/separating direction D1 with regard to the first plate wall 213.

When the voice coil 216 is energized with an alternating signal, the magnetic circuit 220 is vibrated in the approaching/separating direction D1 with regard to the first plate wall 213. Further, the casing 210 is also vibrated under counter-action of the vibration of the voice coil 216 via the damper 230. In this manner, energization of the voice coil 216 causes a relative vibration between the casing 210 and the magnetic circuit 220 in each of the vibration units 20A and 20B. This relative vibration results in vibration of the vibration units 20A and 20B together with the casing 210. Furthermore, in the casing 210, local vibration is caused in the first plate wall 213 to which the voice coil 216 is fixed, the voice coil 216 being counteracted by the magnetic circuit 220. This vibration of the first plate wall 213 causes sounds. As such, the vibration units 20A and 20B are vibrated together with the casing 210 via the relative vibration between the casing 210 and the magnetic circuit 220 by energization of the voice coil 216, wherein the vibration units 20A and 20B then emit sounds.

Figure 4:
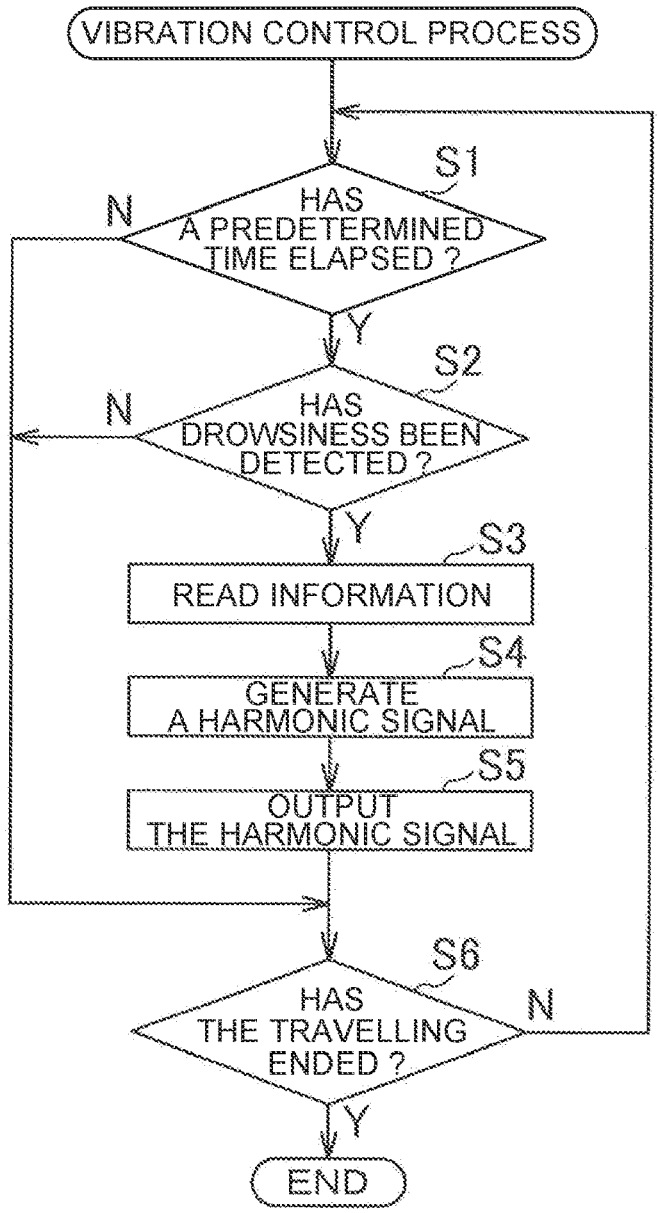
FIG. 4 is a flowchart illustrating an exemplary vibration control process which is performed by the vibration control device.

Here, an exemplar vibration control process which is performed by the harmonic signal generating section 2 will be described with reference to a flowchart according to FIG. 4. The harmonic signal generating section 2 starts the vibration control process when the moving body has begun to travel (or e.g. an engine or a motor has been started which is a power source for the moving body). First in the vibration control process, the harmonic signal generating section 2 determines whether or not a predetermined time has elapsed after beginning the travel (step S1). If the predetermined time has elapsed after beginning the travel (Y in step S1), the harmonic signal generating section 2 determines whether or not the drowsiness detecting section 3 has detected drowsiness of the user (step S2).

If the drowsiness detecting section 3 has detected drowsiness of the user (Y in step S2), the harmonic signal generating section 2 reads information out of the setting section 4 (step S3), generates the harmonic signals (step S4), and outputs it (step S5). If the predetermined time has not elapsed from beginning the travel (N in step S1), if the drowsiness detecting section 3 has not detected drowsiness of the user (N in step S2), or after step S5, the harmonic signal generating section 2 determines whether or not the moving body has ended travelling (step S6). If the moving body has ended travelling (Y in step S6), the harmonic signal generating section 2 ends the vibration control process. If the moving body is still continuing to travel (N in step S6), the vibration control process returns to step S1.

The harmonic signal generating section 2 may determine various parameters for the harmonic signals in steps S4, S5, depending on the drowsiness information and/or the vibration duration. This means that, if the user feels very drowsy, the harmonic signals may be generated e.g. with an increased amplitude and/or with a lower frequency to enable stronger stimulation. Furthermore, since the user gets used to the vibration if the vibration duration is long, various parameters for the harmonic signal to be output may be varied in time.

Figure 5:
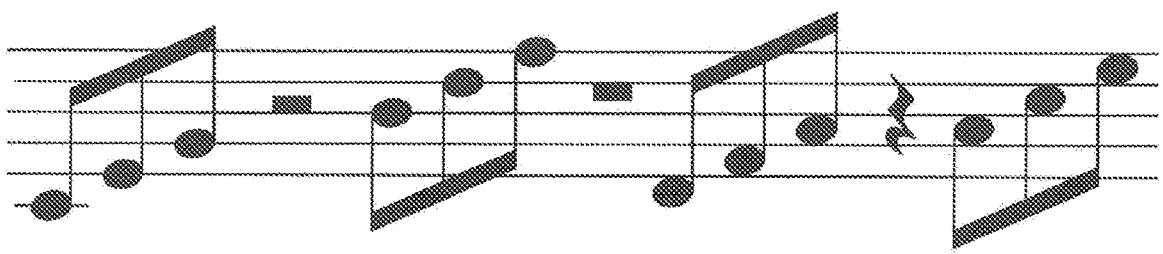
FIG. 5 shows a plurality of alternating signals on a music score, the plurality of alternating signals being output by an output section of the vibration control device.

An example for varying the various parameters for the harmonic signal in time is shown in FIG. 5. FIG. 5 represents the plurality of alternating signals on a music score under the assumption that they would be considered as signals for audio. In the shown example, a group of harmonic signals includes three alternating signals corresponding to a triad, wherein four groups of harmonic signals are arranged in total with pauses between these groups. First harmonic signals have a different combination of frequencies of alternating signals from that of second harmonic signals, wherein following harmonic signals have different combinations of frequencies in a similar manner. This means that the combination of frequencies of the alternating signals are randomly varied in time.

Furthermore, a rest between the first and the second harmonic signals has a different length from a rest between the second and the third harmonic signals, wherein following rests have different rests similarly. This means that a length of the pause periods between the harmonic signals are varied randomly.

Each of the plurality of alternating signals which form the harmonic signals has a frequency of 40 to 120 Hz and a duration of 100 to 200 msec.

Each of the plurality of alternating signals which form the harmonic signals may have a substantially constant amplitude (i.e. a sinusoidal waveform), or may have a waveform of the amplitude which is large at a rising sound and attenuated over time.

Figure 6:
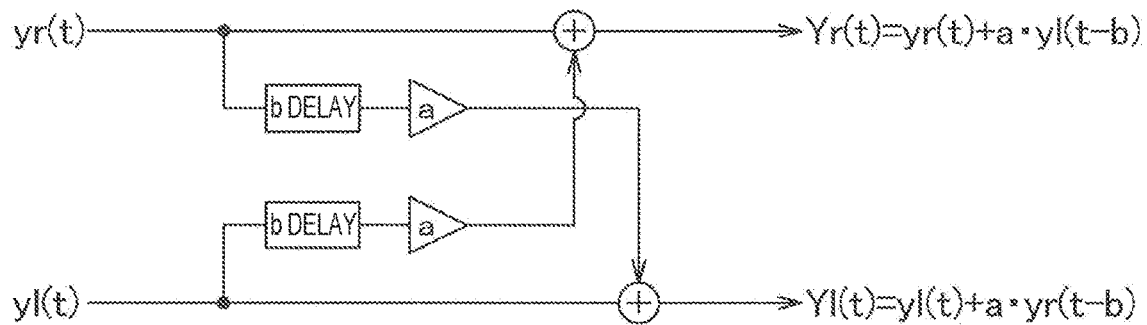
FIG. 6 is a circuit diagram illustrating a mixing circuit for use in the vibration control device.

Furthermore, same harmonic signals may be output to both of the vibration units 20A and 20B, or different harmonic signals may be output to the vibration units 20A and 20B, as described later. In case that different harmonic signals are output to the two vibration units 20A and 20B, e.g. a mixing circuit as shown in FIG. 6 may be used to generate harmonic signals which are correlated to each other.

A function indicative of a main signal for a right vibration unit 20A is designated with yr(t), while a function of a main signal for a left vibration unit 20B is designated with yl(t). For the right main signal yr(t), the left main signal yl(t) is delayed by a time b, amplified in amplitude by a factor of a (0<a1), and then superposed on the right main signal yr(t) to generate a right composite signal Yr(t). The right composite signal Yr(t) is output to the right vibration unit 20A. Furthermore, for the left main signal yl(t), the right main signal yr(t) is delayed by a time b, amplified in amplitude by a factor of a (0<a1), and then superposed on the left main signal yl(t) to generate a left composite signal Yl(t). The left composite signal Yl(t) is output to the left vibration unit 20B.

It is to be noted that a method for generating harmonic signals correlated to each other is not limited to a method using a mixing circuit as described above. For example, harmonic signals correlated to each other may be generated by converting one harmonic signal (monaural signal) into a pseudo-stereo through a pseudo-stereo device and thereby generating two harmonic signals.

With such a configuration, frequencies of the plurality of alternating signals to be successively output have a frequency ratio which is represented with the predetermined integer ratio, so that the resulting vibration from the plurality of alternating signals may awaken the user more easily and make it difficult to give discomfort to the user.

Furthermore, the harmonic signal is output when the drowsiness information is acquired by the drowsiness detecting section 3, so that the vibration can be generated as necessary and it can be difficult to give discomfort to the user. Moreover, the vibration is generated only when the user feels drowsy, so that it can be avoided that the user gets used to the vibration.

Further, each of the plurality of alternating signals which form the harmonic signals has a frequency of 40 to 120 Hz, so that an adequate depth of vibration is achieved with which the alternating signals are transferred into a body of the user, which may make it difficult to give discomfort to the user.

Furthermore, by randomly varying the combination of frequencies of the harmonic signals and/or the length of the pause period, it is possible to suppress that the user gets used to the vibration, and it is possible to maintain the awakening effect for a longer time.

Second Embodiment

Figure 7:
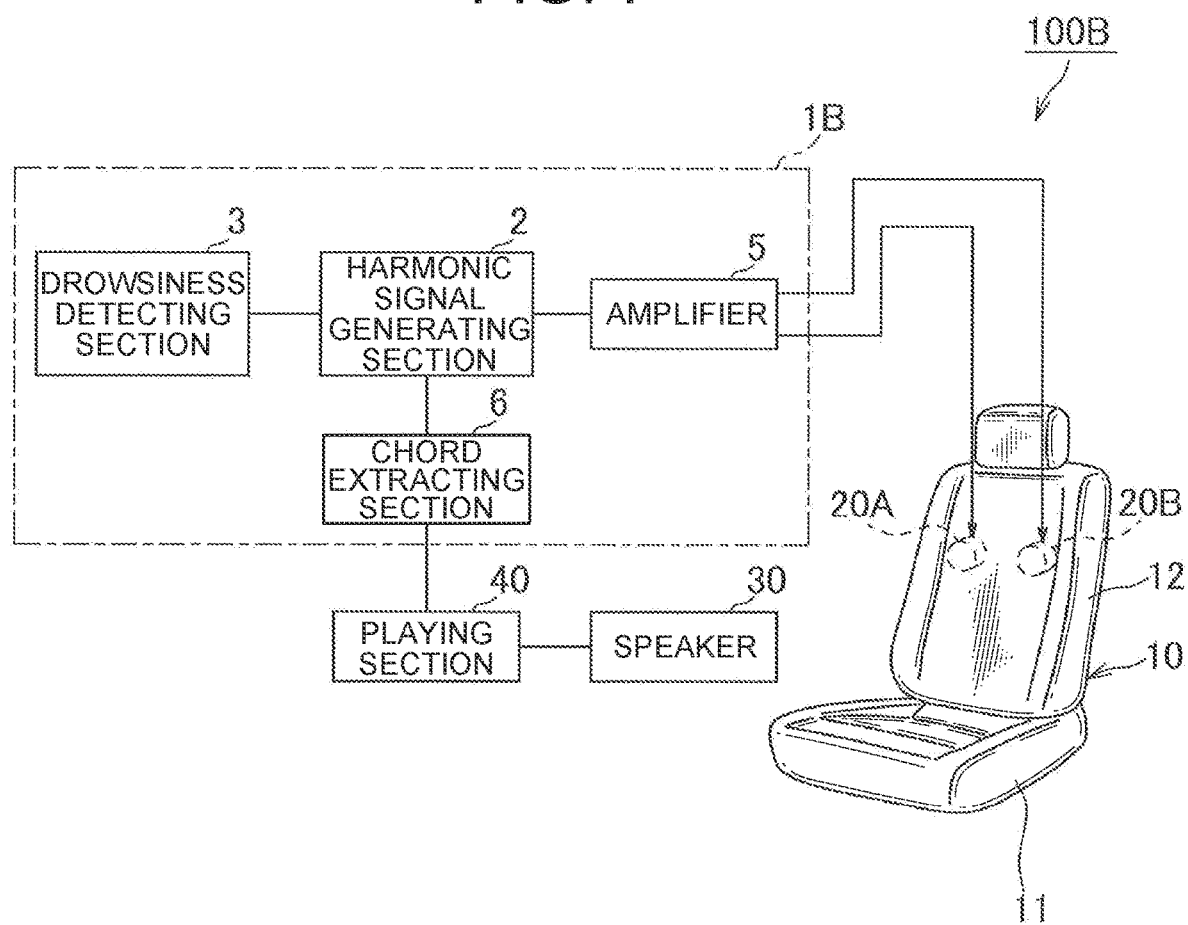
FIG. 7 is a block diagram schematically illustrating a vibration control device according to a second example of the present invention.

As shown in FIG. 7, a vibration control device 1B according to the present example includes a harmonic signal generating section 2 as an output section, a drowsiness detecting section 3 as an acquisition section, an amplifier 5, and a chord extracting section 6, wherein the vibration control device 1A is configured to control two vibration units 20A and 20B which are disposed in a seat 10 of a moving body (vehicle). The vibration control device 1B and the two vibration units 20A, 20B constitute a vibration generating device 100B. It is to be noted that the vibration control device 1B may include a setting section 4.

The chord extracting section 6 is configured to acquire information about a music piece being currently played, from a playing section 40 which is configured to output a signal to a speaker 30 installed on a moving body. This means that the chord extracting section 6 acquires information about the music piece to which the user in a seat 10 is listening (in other words, a music piece which is currently played around the vibration units 20A and 20B). The chord extracting section 6 is further configured to extract a chord included in the music piece from the acquired information. It is sufficient e.g. if the playing section 40 is a car stereo equipment. Furthermore, the chord extracting section may include a sound collecting section (e.g. a microphone) configured to collect sounds emitted from the speaker 30, wherein the chord extracting section may be configured to collect sounds and extract a chord.

The harmonic signal generating section 2 generates a harmonic signal based on the chord extracted by the chord extracting section 6. When all component sounds of the extracted chord are included within a predetermined frequency range (40 to 120 Hz in the present example), the harmonic signals is generated with the plurality of alternating signals having same frequencies as the respective component sounds.

On the other hand, when the extracted chord has a component sound which is not included within the predetermined frequency range, the harmonic signal generating section 2 converts the frequencies of all the component sounds of the extracted chord with a same rate so that the converted component sounds are included within the predetermined frequency range. For example, in case that the component sounds have a frequency of 130 Hz, 164 Hz, and 196 Hz, respectively, all the frequencies are divided by two to convert them into a frequency of 65 Hz, 82 Hz and 98 Hz, respectively. Then, the harmonic signals are formed by the plurality of alternating signals having the converted frequencies respectively. In this manner, the harmonic signal generating section 2 generates the harmonic signals so as to maintain the frequency ratio of the component sounds of the chord extracted by the chord extracting section 6, and to simultaneously include the individual frequencies within the predetermined frequency range.

For the harmonic signals, a plurality of alternating signals is successively output similarly to the first example, wherein they may be output in any sequence. Furthermore, in case that the chord included in the music piece is played by arpeggio, the plurality of alternating signals which form the harmonic signals are preferably output in a same sequence as the music piece. However, a different sequence may be used.

Figure 8:
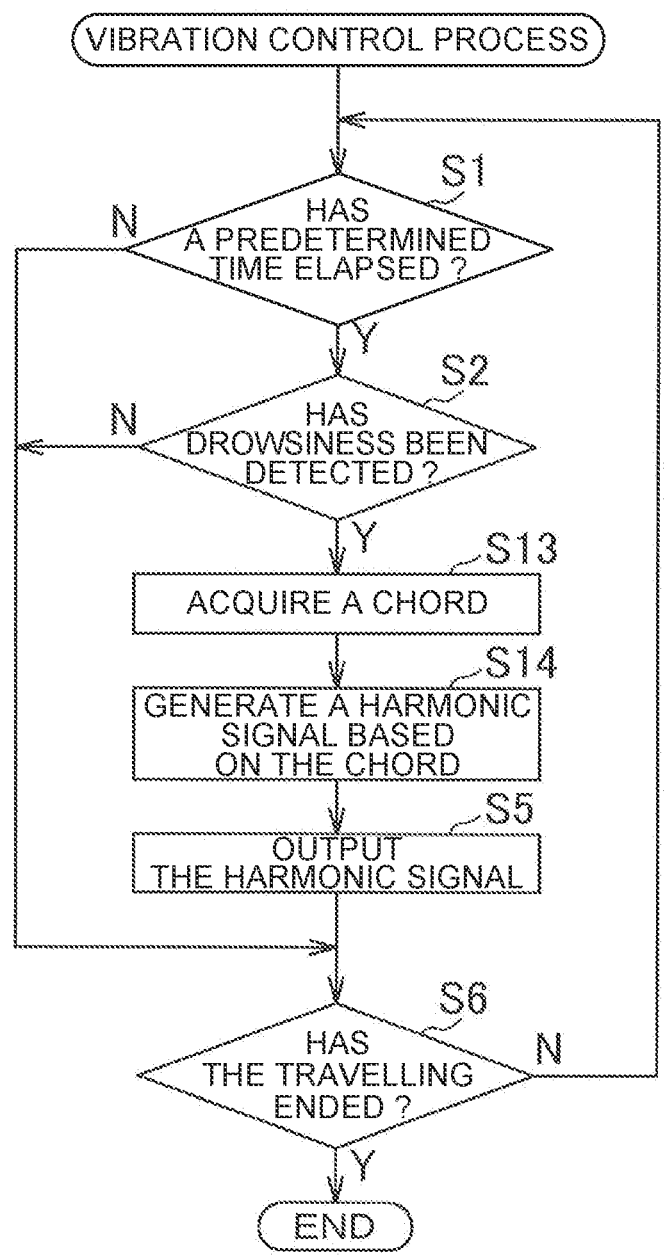
FIG. 8 is a flowchart illustrating an exemplary vibration control process which is performed by the vibration control device.

An exemplar vibration control process which is performed by the harmonic signal generating section 2 according to the present example will be described with reference to a flowchart according to FIG. 8. The vibration control process performed by the harmonic signal generating section 2 according to the present example include common steps with the steps S1, S2, S5 and S6 of the vibration control process according to the first example, wherein the vibration control process according to the present example includes steps between steps S2 and S5 which are different from the steps S3 and S4. It is to be noted that description of the common steps S1, S2, S5 and S6 with the first example will be omitted. In the vibration control process according to the present example, the step S3 is replaced by a step for acquiring a chord from the chord extracting section 6 (step S13). Furthermore, the step S4 is replaced by a step for generating the harmonic signal based on the acquired chord (step S14). This means that in the vibration control process according to the present example, the harmonic signal is generated based on the chord extracted by the chord extracting section 6, although in the vibration control process according to the first example, the harmonic signal is generated based on the information which is previously stored or set in the setting section 4.

Furthermore, similarly to the first example, same harmonic signals may be output to both of the vibration units 20A and 20B, or different harmonic signals may be output to the vibration units 20A and 20B, e.g. by means of a mixing circuit. Alternatively and/or additionally, in case that stereo signals for L and R channels can be acquired from the playing section 40, a harmonic signal associated with an audio signal for the L channel may be output to the vibration unit 20B, wherein a harmonic signal associated with an audio signal for the R channel may be output to the vibration unit 20A.

With such a configuration, frequencies of the plurality of alternating signals to be successively output correspond to the respective frequencies of component sounds of a consonance, so that the resulting vibration from the plurality of alternating signals may awaken the user more easily and make it difficult to give discomfort to the user. Furthermore, since the harmonic signal is generated based on the chord included in a music piece, an impression of the music piece may not be spoiled easily. Moreover, since the chord included in the music piece is varied with the progress of the music piece, a vibration pattern will be varied depending on it. The variation of the vibration pattern may suppress that the user gets used to the vibration, and it is possible to maintain the awakening effect for a longer time.

Furthermore, the harmonic signal is output when the drowsiness information is acquired by the drowsiness detecting section 3, so that the vibration can be generated as necessary, and it can be difficult to give discomfort to the user. Moreover, the vibration is generated only when the user feels drowsy, so that it can suppress that the user gets used to the vibration.

Further, each of the plurality of alternating signals which form the harmonic signals have a frequency of 40 to 120 Hz, so that an adequate depth of the vibration is achieved with which the alternating signals are transferred into a body of the user, which may make it difficult to give discomfort to the user.

It is to be noted that the present invention is not limited to the examples as described above, but includes other configurations etc. which can achieve objectives of the present invention, wherein the present invention includes variations etc. as shown below.

For example, although the harmonic signal according to the first and the second example is output to generate the vibration when the drowsiness information is acquired by the drowsiness detecting section 3, the vibration may be generated for other events. For example, for generating the vibration, it may be determined whether or not the user is driving carelessly. Further, the vibration may be generated when a driving duration exceeds a predetermined duration. Furthermore, the vibration may be generated depending on road information about a road on which the moving body is travelling. In this case, the vibration may be generated e.g. when the moving body is travelling on a monotone road, such as a highway, and/or when a traffic jam has occurred on the road.

Further, although according to the first and the second example, each of the plurality of alternating signals which form the harmonic signals has a frequency of 40 to 120 Hz, the plurality of alternating signals may have values outside this range. While the frequencies of the plurality of alternating signals outside the range of 40 to 120 Hz may give discomfort to the user, this may increase the awakening effect. Therefore, when stronger stimulation is needed, e.g. when the user feels very drowsy and/or when the vibration is continued for a longer duration, the frequencies of the plurality of alternating signals may be outside the range of 40 to 120 Hz.

Furthermore, according to the first example, the combination of frequencies of the plurality of alternating signals is randomly varied in time, and/or the length of the pause period is randomly varied. However, these parameters may not be variable in time, but constant.

Moreover, although the vibration units 20A and 20B constituting the vibration generating device 100A, 100b according to the first and the second example are configured to be installed in the seat 10, the vibration units 20A and 20B may be installed at any position which enables the vibration units 20A and 20B to transmit the vibration to the user. For example, the vibration units 20A and 20B may be provided inside a steering wheel.

Furthermore, according to the second example, when the extracted chord has a component sound which is not included within the predetermined frequency range, all frequencies of component sounds of the chord are converted with a same rate to generate the harmonic signal. However, the harmonic signal generating section 2 may be configured to generate the harmonic signal always without converting component sounds of the extracted chord.

Results of Experiments with Various Signals

The vibration units provided within a seat were driven by means of various signals to evaluate the awakening effect and comfort for sitting people. Subjects were fourteen adult men with an average age of 44.3. Evaluation was conducted for a case using the harmonic signals as an example of the present invention, a case using sinusoidal signals with a single frequency as a conventional case, and a case using a random signal as a reference for comparison. Average amounts of vibration per unit time were the same for these cases.

The harmonic signal according to the example of the present invention was constituted from alternating signals of 65 Hz (corresponding to C), 82 Hz (corresponding to E), and 98 Hz (corresponding to G). Each of the alternating signals had a duration of one second, and is output in the above sequence. Furthermore, after outputting the three alternating signals successively, a pause period was provided for three seconds, and then the three alternating signals were successively output again, which was repeated for 120 seconds.

The sinusoidal signal for the conventional case was constituted from a sinusoid of 82 Hz (corresponding to E). A duration of three seconds and a pause period of three seconds were alternated repeatedly for 120 seconds.

The random signal according to the reference for comparison was formed from the harmonic signal according to the example by replacing the alternating signal of 82 Hz with an alternating signal of 92 Hz (F #).

Figure 9:
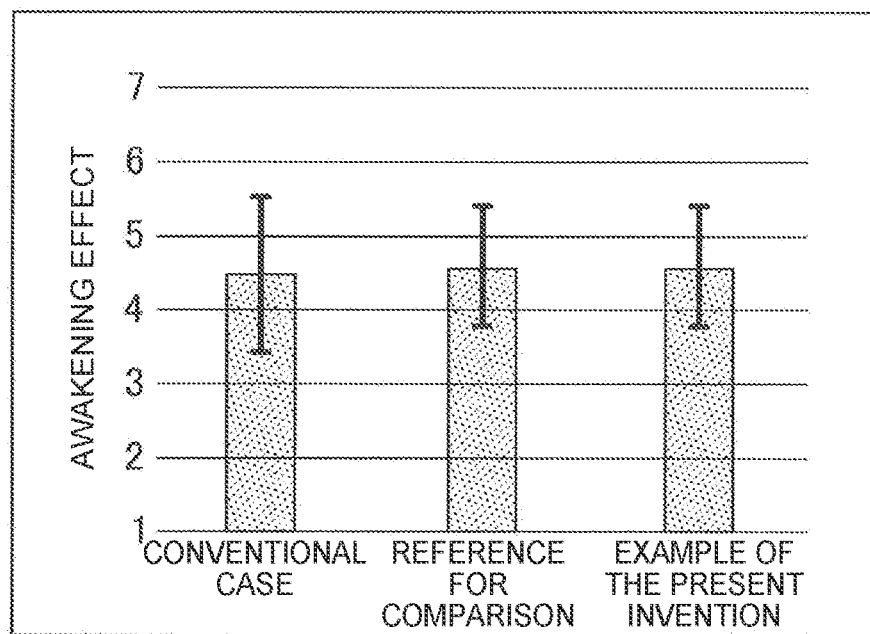
FIG. 9 is a graph showing an experimental result of an awakening effect which is obtained from vibration.
Figure 10:
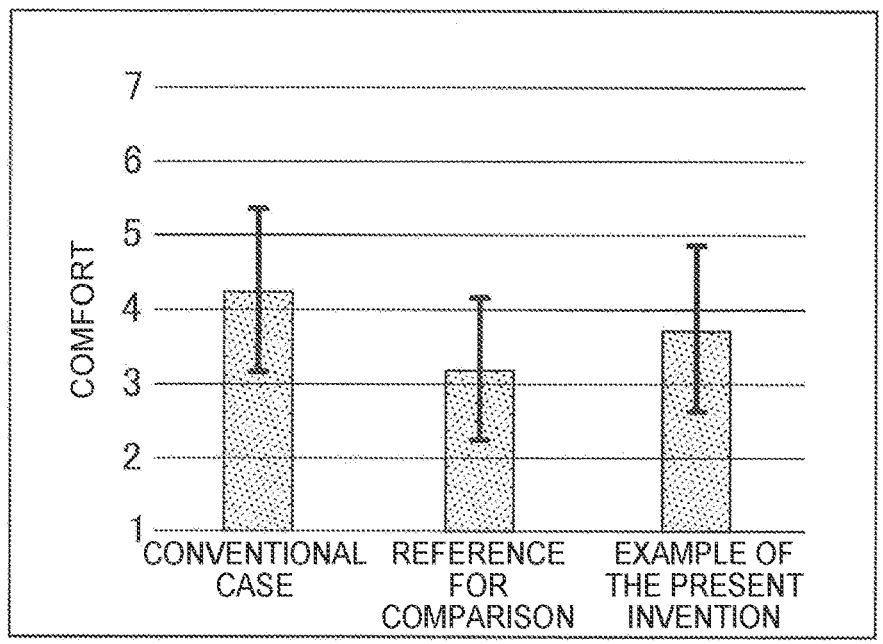
FIG. 10 is a graph showing an experimental result of comfort which is obtained by the vibration.

The subjects subjectively evaluated the awakening effect and comfort for the vibrations generated with the various signals, wherein a full score was set to seven points. FIG. 9 shows a result about the awakening effect, while FIG. 10 shows a result about the comfort.

For the awakening effect, 4.48 was given for the conventional case, 4.61 for the reference, and 4.59 for the example. This means that the increased awakening effect was observed for the reference and the example than for the conventional case. For the comfort, 4.25 was given for the conventional case, 3.20 for the reference, and 3.75 for the example. This means that the reduced comfort was observed for the reference and the example, however, the comfort was reduced by a less amount for the example than for the reference.

Although the best configuration, method etc. for implementing the present invention are disclosed in the above description, the present invention is not limited thereto. Namely, while the present invention is particularly shown and described mainly with regard to the specific examples, the above mentioned examples may be modified in various manners in shape, material characteristics, amount or other detailed features without departing from the scope of the technical idea and purpose of the present invention. Therefore, the description with limited shapes, material characteristics etc. according to the above disclosure is not limiting the present invention, but merely illustrative for easier understanding the present invention so that the description using names of the elements without a part or all of the limitations to their shapes, material characteristics etc. is also included in the present invention.

REFERENCE SIGNS LIST

1A Vibration control device
2 Harmonic signal generating section (output section)
3 Drowsiness detecting section (acquisition section)
5 Amplifier (output section)
20A, 20B Vibration units
100A Vibration generating device
10 Seat
11 Seat surface section
12 Backrest section

What is claimed is:

1. A vibration control device configured to control a vibration unit which is configured to generate vibration to be transferred to a user, the vibration control device comprising:
an output section configured to output groups of signals including alternating signals with multiple frequencies as driving signals to drive the vibration unit, the multiple frequencies in each of the groups of signals being represented with a frequency ratio between component sounds of a consonance, signals in each of the group of signals being successively output,
wherein, when outputting a second one of the groups of signals next to a first one of the groups of signals, the output section is configured to vary a combination of the alternating signals with multiple frequencies included in the second one of the groups of signals from a combination of the alternating signals with multiple frequencies in the first one of the groups of signals, and
the vibration control device is configured to control the vibration unit that is configured to generate the vibration to be transferred to one or more of a back, a hand, and a lower body of the user.

2. The vibration control device according to claim 1, further comprising:
an acquisition section configured to acquire drowsiness information of the user,
wherein the output section is configured to output the driving signals when the drowsiness information is acquired by the acquisition section.

3. A vibration generating device comprising:
the vibration control device according to claim 2; and
at least one vibration unit.

4. The vibration control device according to claim 1, wherein each of the alternating signals has a frequency of 40-120 Hz.

5. A vibration generating device comprising:
the vibration control device according to claim 4; and
at least one vibration unit.

6. The vibration control device according to claim 1, wherein the output section is configured to randomly vary a combination of frequencies of alternating signals included in each of the groups of signals in time.

7. A vibration generating device comprising:
the vibration control device according to claim 6; and
at least one vibration unit.

8. The vibration control device according to claim 1, wherein the output section is configured to output the groups of signals with a pause period interposed between the groups of signals and to randomly vary a length of the pause period.

9. A vibration generating device comprising:
the vibration control device according to claim 8; and
at least one vibration unit.

10. A vibration generating device comprising:
the vibration control device according to claim 1; and
at least one vibration unit.

11. The vibration generating device according to claim 10, wherein the vibration unit is provided inside a seat surface section or a backrest section of a seat in which the user is seated.

12. The vibration generating device according to claim 10, wherein the at least on vibration unit comprises a plurality of vibration units,
wherein the output section is configured to output the driving signals to each of the plurality of vibration units, the driving signals being different from each other and correlated to each other.

13. A vibration control method for controlling a vibration unit which is configured to generate vibration to be transferred to a user, the method comprising:
outputting groups of signals including alternating signals with multiple frequencies which are driving signals to drive the vibration unit, the multiple frequencies in each of the groups of signals being represented with a frequency ratio between component sounds of a consonance, signals in each of the group of signals being successively output, the outputting including varying a combination of the alternating signals with multiple frequencies included in a second one of the groups of signals from a combination of the alternating signals with multiple frequencies in a first one of the groups of signals, the second one of the groups of signals being output next to the first one of the groups of signals, and the vibration control device is configured to control the vibration unit that is configured to generate the vibration to be transferred to one or more of a back, a hand, and a lower body of the user.

14. A vibration control program which is configured to cause a computer to execute the vibration control method according to claim 13.

15. A non-transitory computer-readable storage medium on which is stored a vibration control program which, when executed by a computer, causes the computer to perform the method of claim 13.

16. The vibration control method according to claim 13, further comprising:
acquiring drowsiness information of the user; and
outputting the driving signals when the drowsiness information is acquired.

* * * * *